US006576228B1

(12) United States Patent
Crookham et al.

(10) Patent No.: US 6,576,228 B1
(45) Date of Patent: Jun. 10, 2003

(54) PERSONAL WASH SUNSCREEN COMPOSITIONS WHICH DEPOSIT AND LATHER WELL

(75) Inventors: Harry Crookham, Lyndhurst, NJ (US); David John Lang, Ossining, NY (US); Mengtao He, Scottsdale, AR (US); Abid Khan-Lodhi, North Bergen, NJ (US)

(73) Assignee: Unilever Home & Personal Care USA division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/523,248

(22) Filed: Mar. 10, 2000

(51) Int. Cl.$^7$ .............................. A61K 7/44; A61K 7/42; A61K 7/06; A61K 7/075; A61K 7/08
(52) U.S. Cl. ..................... 424/60; 424/59; 424/70.9; 424/70.19; 424/70.22; 424/400; 424/401; 510/119; 510/130; 510/137; 510/141; 510/158; 510/159
(58) Field of Search ................ 424/400, 401, 424/59, 60, 70.9, 70.19, 70.22; 510/119, 130, 137, 141, 158, 159

(56) References Cited

U.S. PATENT DOCUMENTS

| 4,701,321 | A |   | 10/1987 | Bernstein |
| 4,933,174 | A |   | 6/1990  | Bernstein |
| 4,976,953 | A | * | 12/1990 | Orr et al. ..................... 424/47 |
| 5,487,884 | A |   | 1/1996  | Bissett et al. |
| 5,981,464 | A | * | 11/1999 | He et al. ..................... 510/451 |
| 6,022,547 | A | * | 2/2000  | Herb et al. .................. 424/401 |
| 6,057,275 | A | * | 5/2000  | Fair et al. ................... 510/151 |
| 6,074,998 | A | * | 6/2000  | He et al. ..................... 510/155 |
| 6,217,852 | B1| * | 4/2001  | Gildenberg et al. ........... 424/59 |
| 6,224,852 | B1| * | 5/2001  | Morgan et al. ............... 424/59 |

FOREIGN PATENT DOCUMENTS

| EP | 0552024       |   | 7/1993  |
| EP | 0583888       |   | 3/1994  |
| FR | 2781369 A1    | * | 4/2000  |
| WO | 96/14053      |   | 5/1996  |
| WO | 00/18367      |   | 4/2000  |
| WO | 00/64406      |   | 11/2000 |

OTHER PUBLICATIONS

International Search Report Application No. PCT/EP 01/02223 mailed Jul. 22, 2001.

* cited by examiner

*Primary Examiner*—Jose' G. Dees
*Assistant Examiner*—Marina Lamm
(74) *Attorney, Agent, or Firm*—Ronald A. Koatz

(57) ABSTRACT

The invention provides personal wash compositions which deposit high levels of sunscreen while maintaining good lather. Enhanced deposition, from bar or liquid, is based on specific sunscreens used, particularly on their solubility.

11 Claims, No Drawings

PERSONAL WASH SUNSCREEN COMPOSITIONS WHICH DEPOSIT AND LATHER WELL

FIELD OF THE INVENTION

The invention relates to personal wash compositions which deposit high levels of sunscreen (SPF >2) while maintaining good lather (i.e., suffer minimal lather degradation over time relative to compositions with more "oily" sunscreens). Enhanced deposition is found from both bar and liquid compositions and is based on the solubility or non-solubility of the sunscreen used.

BACKGROUND OF THE INVENTION

It is a difficult task to deposit significant levels of sunscreen from skin cleansers. Moreover, most sunscreens severely defoam the cleanser composition. Therefore, previous attempts to deliver sunscreen from cleansers resulted in cleanser having low levels of protection (i.e., SPF <2); which had unsatisfactory user properties (e.g., low lather); and which were expensive to make (because of high levels of sunscreen required to obtain effective protection).

One reason deposition has been so difficult to achieve is that most of sunscreens used are either water insoluble oils or insoluble fine solid particles (e.g., ZnO, $TiO_2$). Such sunscreens are generally dispersed into dilute suspensions by surfactants present in the cleanser. As a result, and without wishing to be bound by theory, it is believed that most of the sunscreen will remain suspended, the suspended sunscreen will be removed when skin is rinsed, and little will be left to deposit on the skin. Further, dispersions of the sunscreens into the wash liquid tends to defoam the liquor. In addition, incorporation of oily sunscreen in bars also generally increases softness, stickiness and mush.

Unexpectedly, applicants have found a novel class of sunscreens which can be delivered and provide superior sun protection. These sunscreens can be deposited even in presence of anionic surfactants. Unlike most sunscreens, these are much more soluble in water than the usual "oily" sunscreen and provide measurable sun protection even at low levels of addition (e.g., 0.1–15%, preferably 0.5 to 12%, more preferably 1.0 to 10% by wt.). Moreover, since they are more soluble in water, they do not defoam cleanser during wash process.

More specifically, applicants have found specific sunscreen agents which are organic molecules absorbing light in the UV range. These sunscreens are water-soluble UV absorbers (greater than or equal to 0.1% preferably greater than 0.5% water solubility on a weight to weight basis at neutral pH). The sunscreens include a functional group that is anionic or at least part of the sunscreen becomes anionic (e.g., anionic functional group incorporated at sufficiently high pH) at suitable pH (e.g., pH $\geq 3$, preferably greater than 4, preferably 4 to 10) and the sunscreens are water soluble or become soluble at suitable pH (again about 3 to 10). Examples of such molecules include: phenylbenzimidazole sulphonic acid, anionic salts of said acid which form at pH of 7 and above and mixtures thereof (forming at pH between 4 and 7); ferulic acid, its anionic salts and mixtures thereof; benzophenone-4, its anionic salts and mixtures thereof; and benzophenone-9, its anionic salts and mixtures thereof. Preferably, the sunscreen agents are used in the form of their salts generally at pH 7 and above.

While not wishing to be bound by theory, these anionic organic sunscreen molecules are believed to bind to positively charged sites on proteins within the skin thereby accounting for enhanced deposition. Because molecules deposited through binding from solution cover the surface uniformly, the UV protection is also believed to be more effective than protection obtained from oily or particulate sunscreens where the deposition may be localized to small areas of skin and leave some areas unprotected. Moreover, because the agents are more soluble in water than oily components, they cause less defoaming than the oily or particulate sunscreen agents. As noted above, oily, particulate sunscreens are believed to suspend in surfactants and more readily wash off when rinsed, thereby leading to lower deposition. Oily agents also lead to mushier bars. The specific sunscreen agents of the invention avoid these problems.

Some of the organic sunscreen materials of the invention are not new. For example, WO 14053 to Cussons Int. Ltd. teaches personal wash compositions containing sunscreen agents including phenylbenzimidazole sulphonic acid (which is recited among a list of sunscreen agents which may be used (page 7).

The reference does not recognize that the sulphonic acid sunscreen agent or salts thereof provide superior sun protection relative to other sunscreens including even those used in the reference itself (see Examples 1–3 of reference). The higher water solubility also makes the sunscreens less defoaming and more soluble for personal wash products where foaming is considered a desirable attribute.

U.S. Pat. Nos. 4,933,174 and 4,701,321 by J. Bernstein (assigned to Amethyst Investment Group, Inc.) teaches a liquid PW composition, which comprises nonionic and amphoteric surfactants, and sunscreen materials including aminobenzoic acid, the esters of an aminobenzoic acid, homosalate, 2-hydroxy-4-methoxylbenzophenone (oxybenzone) or 2-ethoxyethyl p-methoxycinnamate (cinoxate). Nonionic and amphoteric surfactants instead of anionic surfactants are used to enhance the deposition of sunscreen agents. Repeated washing and bathing with the compositions leaves a long-lasting layer of sunscreens in the stratum corneum of the skin. The reference fails to recognize that specific anionic sunscreens (e.g., anionic salts) of the invention, particularly when used in systems comprising anionic surfactants, deposit better than other sunscreens.

The noted U.S. patents also do not specifically include phenylbenzimidazole sulphonic acid, benzophenone-4 or any of the other materials suitable for our invention as candidates for the sunscreen agents claimed. These patents further require that formulations contain only nonionic or amphoteric surfactant and further requires that the compositions be used repeatedly over many weeks to achieve the claimed effects.

BRIEF SUMMARY OF THE INVENTION

Unexpectedly, applicants have found that when specific sunscreens and/or their salts are used in personal wash compositions, they are more water soluble than many oily particulate sunscreens normally used (e.g., "normal" oils having solubility of less than 0.1% wt. by wt. water compared to more soluble "salts" of subject invention); they provide enhanced sun protection factor or SPF (e.g. SPF greater than 2, to about 25, preferably greater than 3 to 20, more preferably from about 4 to 15); and the sunscreen does not depress foaming (e.g., foaming does not depress over time compared with more oily components whose lather does depress more quickly over time).

Generally, using the sunscreens of invention, foaming does not depress more than about 50%, preferably more than 30%, preferably more than about 25% over 30 minutes time using test as defined in examples.

More specifically, the present invention provides a personal wash composition, particularly personal wash compositions which may be in bar or liquid form. In one embodiment the compositions are bars comprising:

(1) 20% to 85% by wt of first anionic surfactant which may be fatty acid soap or a synthetic anionic;
(2) 0–25%, preferably 1–20% second surfactant selected from the group consisting of second anionic surfactant (different from first), nonionic, amphoteric, cationic and mixture thereof;
(3) 0–15% free fatty acid;
(4) 0–20% water soluble structurant (e.g., polyalkylene glycol, EO-PO copolymers);
(5) 0 to 40%, preferably 0–35% alkanoate (e.g., glycerol monostearate) having chain length of $C_{12}$ to $C_{24}$; and
(6) 0.1 to 10% of a sunscreen agent, anionic salt (e.g., functional group attached to sunscreen agent which, in solution, yields negative charge such as, for example, sulfates, sulfonates, carboxylates, phosphates, phosphonates, etc.), or mixtures thereof (at least some portion of the sunscreen must be in its salt form; however, this is inherently accomplished by specifying minimum pH values);
wherein sunscreen agent (by which is meant overall equilibrium of the acid form of the sunscreen, its salt and mixtures) has a water solubility of greater than or equal to 0.1%, preferably greater than 0.5% on weight to weight basis as measured at pH 7;
wherein said sunscreen has SPF of greater than 2 to 25; and
wherein composition does not degrade more than 50% lather, preferably no more than 35%, more preferably no more than 25% over 30 minutes as defined in examples.

Bars generally will have 1–15%, preferably 2–12% water.

In a second embodiment, composition may be liquid composition comprising:

(1) 10–80% anionic surfactant;
(2) 0–25% of second surfactant selected from group consisting of anionic different from first, nonionic, amphoteric/zwifterionic, cationic and mixtures thereof; and
(3) 0.1 to 10% of a sunscreen agent, salt thereof or mixtures as defined above;
wherein sunscreen agent has a water solubility of greater than or equal to 0.1%, preferably greater than 0.5% on weight to weight basis as measured at pH 7;
wherein said sunscreen has SPF of greater than 2 to 25; and
wherein composition does not degrade more than 50% lather, preferably no more than 35%, more preferably no more than 25% over 30 minutes as defined in examples.

DETAILED DESCRIPTION OF THE INVENTION

The present invention is based on applicants unexpected finding that certain sunscreen agents and/or salts thereof are anionic, water-soluble compounds which provide enhanced SPF while simultaneously not depressing foam relative to more oily, less water soluble sunscreen compounds (e.g., those which are generally less soluble and have solubility of less than 0.5% wt. for wt. water). These "more" water-soluble sunscreen agents and/or anionic salts thereof (counterions may exist to anionic group as well) provide unexpectedly enhanced effect whether used in bar or liquid cleanser compositions.

In one embodiment, the invention comprises bar compositions comprising:

(1) 20 to 85% by wt. of a first anionic surfactant which is fatty acid soap or synthetic anionic;
(2) 0 to 25% by wt. of a second surfactant selected from the group consisting of a second anionic (differing from the first), nonionic surfactant, amphoteric/zwitterionic surfactant, cationic surfactant and mixtures thereof;
(3) 0 to 15% by wt. free fatty acid (particularly where bar is a predominantly fatty acid soap bar);
(4) 0 to 20% of a water-soluble structurant which is neither soap nor non-soap detergent and has MW in the range 40 to 100° C. (e.g., polyalkylene glycol EO-PO copolymers);
(5) 0 to 40% glycerol monoalkanoate of $C_{12}$–$C_{24}$ chain length; and
(6) 0.1 to 10% of a sunscreen agent and/or salt thereof (providing anionic charge) wherein sunscreen and/or salt thereof has SPF greater than 2 to 25, preferably greater than 3 to 20, more preferably greater than about 4 to 15;
wherein sunscreen agent and/or salt has solubility of greater than or equal to 0.1%, preferably greater than 0.5% on weight to weight basis as measured neutral pH; and
wherein sunscreen agent and/or salt has lather which does not substantially degrade over time relative to more oily components.

In second embodiment of the invention, compositions may be liquid cleanser comprising:

(1) 10–80% first anionic surfactant; and
(2) 0 to 25% second surfactant selected from the group consisting of anionic different from first, nonionic, amphoteric/zwitterionic, cationic and mixtures thereof;
(3) 0.1 to 10% of sunscreen and/or salt thereof as defined with bar compositions thereof; and
(4) balance water,
wherein compositions has SPF values, solubility and lather parameters as defined for bar compositions above.

Each of these embodiments is described in more detail below.

Bar Compositions

First Anionic

The first anionic surfactant may be a synthetic surfactant or fatty acid soap. Although not preferred, the bar compositions may comprise a "pure" soap composition. Such bars are generally not mild (although they do foam well and have sensory properties preferred by some consumers) and so it is generally preferred to use bars which are predominantly synthetic or which are combinations of synthetic and soap.

The term "soap" is used here in its popular sense, i.e., the alkali metal or alkanol ammonium salts of aliphatic alkane- or alkene monocarboxylic acids. Sodium, potassium, mono-, di and tri-ethanol ammonium cations, or combinations thereof, are suitable for purposes of this invention. In general, sodium soaps are used in the compositions of this invention, but from about 1% to about 25% of the soap may be potassium soaps. The soaps useful herein are the well known alkali metal salts of natural or synthetic aliphatic (alkanoic or alkanoic) acids having about 12 to 22 carbon atoms, preferably about 12 to about 18 carbon atoms. They may be described as alkali metal carboxylates of acrylic hydrocarbons having about 12 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. The proportion will be greater when mixtures of coconut oil and fats such as tallow, palm oil or non-tropical nut oils or fats are used, wherein the principle chain lengths are $C_{16}$ and higher. Preferred soap for use in the compositions of this invention has at least about 85% fatty acids having about 12–18 carbon atoms.

Coconut oil employed for the soap may be substituted in whole or in part by other "high-lauric" oils, that is, oils or fats wherein at least 50% of the total fatty acids are composed of lauric or myristic acids and mixtures thereof. These oils are general exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 15% to about 20% coconut oil and about 80% to about 85% tallow. These mixtures contain about 95% fatty acids having about 12 to about 18 carbon atoms. The soap may be prepared from coconut oil in which case the fatty acid content is about 85% of $C_{12}$–$C_{18}$ chain length.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric ($C_{12}$), myristic ($C_{14}$), palmitic ($C_{16}$) or staric ($C_{18}$) acids with an alkali metal hydroxide or carbonate.

The first anionic detergent active which may be used may be aliphatic sulfonates, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxy alkane sulfonate or alkyl glycerol ether sulfonate (AGS); or aromatic sulfonates such as alkyl benzene sulfonate.

The first anionic may also be an alkyl sulfate (e.g., $C_{12}$–$C_{18}$ alkylsulfate) or alkyl ether sulfate (including alkyl glycerol ether sulfates). Among the alkyl ether sulfates are those having the formula:

$$RO(CH_2(CH_2-O)_nSO_3M$$

wherein R is an alkyl or alkenyl having 8 to 18 carbons, preferably 12 to 18 carbons; n has an average value of greater than 1.0, preferably greater than 3: and M is a solubilizing cation such as sodium, potassium ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, alkyl glycosides and acyl isethionates.

Sulfosuccinates may be monoalkyl sulfosuccinates having the formula:

$$R^4O_2CCH_2CH(SO_3M)CO_2M;$$

and amide-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation.

Sarcosinates are generally indicated by the formula $$RCON(CH_3)CH_2CO_2M,$$

wherein R ranges from $C_8$–$C_{20}$ alkyl and M is a solubilizing cation.

Taurates are generally identified by formula:

$$R^2CONR^3CH_2CH_2SO_3M$$

wherein $R^2$ ranges from $C_8$–$C_{20}$ alkyl, $R^3$ ranges from $C_1$–$C_4$ alkyl and M is a solubilizing cation.

Particularly preferred are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 10% to about 70% by weight of the total composition. Preferably, this component is present from about 30% to about 60%.

The acyl isethionate may be an alkoxylated isethionate such as is described in Ilardi et al., U.S. Ser. No. 796,748, hereby incorporated by reference. This compound has the general formula:

$$RC(=O)-O-CH(X)-CH_2-(OCH(Y)-CH_2)_{\overline{m}}-SO_3^-M^+$$

wherein R is an alkyl group having 8 to 18 carbons, m is an integer from 1 to 4, X and Y are hydrogen or an alkyl group having 1 to 4 carbons and $M^+$ is a monovelent cation such as, for example, sodium, potassium or ammonium.

In general the anionic component will comprise from about 10 to 70% of the composition, preferably 20–50% by wt. of the composition.

Second Surfactant

The second surfactant may be any of the anionics defined above except that it differs from the first anionic. The second component may also be any of the amphoteric or nonionics discussed below as well as a mixture of the anionic, amphoteric and/or nonionic.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

$$R^1-[C(=O)-NH(CH_2)_{\overline{m}}]_n-N^+(R^2)(R^3)-X-Y$$

wherein
$R^1$ is alkyl or alkenyl of 7 to 18 carbon atoms: $R^2$ and $R^3$ are each independently alkyl, hydroxyalkyl or carboxyalkyl of 1 to 3 carbon atoms;
m is 2 to 4;
n is 0 to 1
X is alkylene of to 3 carbon atoms optionally substituted with hydroxyl, and
Y is $-CO_2-$ or $-SO_3-$ Suitable amphoteric detergents within the above general formula include simple betaines of formula:

$$R^1-N^+(R^2)(R^3)-CH_2CO_2^-$$

and amido betaines of formula:

$$R^1-CONH(CH_2)_{\overline{m}}-N^+(R^2)(R^3)-CH_2CO_2^-$$

where m is 2 or 3;

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula:

$$R^1-N^+(R^2)(R^3)-(CH_2)_3SO_3^- \quad \text{or}$$

$$R^1-CONH(CH_2)_m-N^+(R^2)(R^3)-(CH_2)_3SO_3^-$$

where m is 2 or 3, or variants of these in which $-(CH_2)_3SO_3-$ is replaced by:

$$-CH_2CH(OH)CH_2SO_3^-$$

In these formula $R^1$, $R^2$ and $R^3$ are as discussed previously.

The nonionic which may be used as the second component of the invention include in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Ser. No. 816,419 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr., which is also incorporated into the subject application by reference.

In general the second component (i.e., second anionic nonionic and/or amphoteric compound or mixture) is incorporated into the composition as less than 20% by weight, preferably 1 to 15% by weight of the composition.

Structurant

In general, bars of the invention may comprise 0 to 75% structurant (e.g., free fatty acid, water soluble structurant, glycerol monoalkanoate noted below). Preferably, the bar will contain 5% to 65% structurant though none is required.

Free Fatty Acid

Free fatty acids of 8–22 carbon atoms may also be desirably incorporated within the compositions of the present invention. Some of these fatty acids are present to operate as superfatting agents and others as skin feel and creaminess enhancers. Superfatting agents enhance lathering properties and may be selected from fatty acids of carbon atoms numbering 8–18, preferably 10–16, generally in an amount up to 15% by weight (although higher amounts may be used) of the composition. Skin feel and creaminess enhancers, the most important of which is stearic acid, are also desirably present in these compositions.

Water Soluble Structurant

Another compound which may be used in the bar is water soluble structurant (e.g., polyalkylene glycol).

This component should comprise 0% by wt. to 60%, preferably greater than 5% to 40% by wt. of the bar composition.

The structurant (e.g., polyalkylene glycol) has a melting point of 40° C. to 100° C., preferably 45° C. to 100° C., more preferably 50° C. to 90° C.

Materials which are envisaged as the water soluble structurant (b) are moderately high molecular weight polyalkylene oxides of appropriate melting point and in particular polyethylene glycols or mixtures thereof.

Polyethylene glycols (PEG's) which may be used may have a molecular weight in the range 1,500–20,000.

It should be understood that each product (e.g., Union Carbide's Carbowax® PEG 8,000) represents a distribution of molecular weights. Thus PEG 8,000, for example, has an average MW range of 7,000–9,000, while PEG 300 has an average MW range from 285 to 315. The average MW of the product can be anywhere between the low and high value, and there may still be a good portion of the material with MW below the low value and above the high value.

In some embodiments of this invention it is preferred to include a fairly small quantity of polyalkylene glycol (e.g., polyethylene glycol) with a molecular weight in the range from 50,000 to 50,000, especially molecular weights of around 100,000. Such polyethylene glycols have been found to improve the wear rate of the bars. It is believed that this is because their long polymer chains remain entangled even when the bar composition is wetted during use.

If such high molecular weight polyethylene glycols (or any other water soluble high molecular weight polyalkylene oxides) are used, the quantity is preferably from 1% to 5%, more preferably from 1% or 1.5% to 4% or 4.5% by weight of the composition. These materials will generally be used jointly with a larger quantity of other water soluble structurant (b) such as the above mentioned polyethylene glycol of molecular weight 1,500 to 10,000.

Some polyethylene oxide polypropylene oxide block copolymers melt at temperatures in the required range of 40° C. to 100° C., and may be used as part or all of the water soluble structurant (b). Preferred ere are block copolymers in which polyethylene oxide provides at least 40% by weight of the block copolymer. Such block copolymers may be used in mixtures with polyethylene glycol or other polyethylene glycol water soluble structurant.

Glycerol Monoalkanoate

Another optional structurant which may be used is glycerol monoalkanoate wherein alkanoate group may be $C_{12}$–$C_{24}$ alkyl (e.g., glycerol monostearate). This may comprise 0–60% by wt. of bar, preferably 5% to 50% by wt.

Sunscreen

The sunscreens of the invention are defined by the fact that they are sunscreens which form salts (at sufficient pH) so that the salts or an equilibrium of salt and the acid form of the sunscreen have a solubility of greater than 0.1% wt/wt., preferably greater than 0.5% as measured at neutral pH. As noted, in general the pH of the composition has to be high enough to have at least some portion of the anionic salt.

The anionic salts are formed by functional anionic groups well known to those skilled in the art such as sulphates, sulfonates, carboxylates, phosphates, phosphonates and other groups which are well known to provide anionic charges in solution.

Unexpectedly, applicants have found that use of these sunscreens and/or salts which have the defined solubility will provide enhanced SPF (e.g., 2 to 25) relative to other sunscreens while at the same time not depressing the lather function of the final composition.

Examples of such sunscreen compounds include phenyl-benzimidazole sulphonic acid and salts thereof; ferulic acid and salts thereof; benzophenone and its salts thereof. Other examples include variants of benzophenone and salts thereof.

Other Compounds

Skin mildness improvers also preferably used in the composition of the invention are salts of isethionate. Effective salts cations may be selected from the group consisting of alkali metal, alkaline earth metal, ammonium, alkyl ammonium and mono-, di or tri-alkanolammonium ions. Specifically preferred cations include sodium potassium, lithium, calcium, magnesium, ammonium, triethylammonium, monoethanolammonium, diethanolammonium or triethanolammonium ions.

Particularly preferred as a mildness improver is simple unsubstituted sodium isethionate.

The skin mildness improver will be present from about 0.5% to about 50%. Preferably, the mildness improver is present from about 1% to about 25%, more preferably from about 2% to about 15, optimally from 3% to 10% by weight of the total composition.

Other performance chemicals and adjuncts may be needed with these compositions. The amount of these chemicals and adjuncts may range from about 1% to about 40% by weight of the total composition. For instance, from 2 to 10% of a suds-busing detergent salt may be incorporated. Illustrative of this type additive are salts selected from the group consisting of alkali metal and organic amine higher aliphatic fatty alcohol sulfates, alkyl aryl sulfonates and the higher aliphatic fatty acid taurinates.

Adjunct materials including germicides, perfumes, colorants, pigments such as titanium dioxide and water may also be present.

The bar compositions of the invention have SPF of greater than 2 to 25, preferably greater than about 3 to 20 and more preferably greater than about 4 to 15.

SPF is defined as per the protocol in the example section.

In addition compositions have lather of which does not degrade more than 50%, preferably more than 35%, preferably more than 25% over 30 minute period.

In a second embodiment, the compositions of the invention may also be liquid compositions as noted above.

Liquid

First Anionic

In the liquid compositions, the first anionic surfactant may be any of the surfactants as for the bars above except that it will not be "soap" as defined therein.

Second Surfactant

The second surfactant may also be one of the above as defined for bars.

Optional

The liquids of this invention may be isotropic single phase liquids or they may be structured as defined and using structurants as defined in U.S. Pat. No. 5,952,286 to Puvvada et al. hereby incorporated by reference into the subject invention.

The compositions may contain oils or emollients as noted below.

Vegetable oils: Arachis oil, castor oil, cocoa butter, coconut oil, corn oil, cotton seed oil, olive oil, palm kernel oil, rapeseed oil, safflower seed oil, sesame seed oil and soybean oil.

Esters: Butyl myristate, cetyl palmitate, decyloleate, glyceryl laurate, glyceryl ricinoleate, glyceryl stearate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, propylene glycol monolaurate, propylene glycol ricinoleate, propylene glycol stearate, and propylene glycol isostearate.

Animal Fats: Acytylatelte lanolin alcohols, lanolin, lard, mink oil and tallow.

Fatty acids and alcohols: Behenic acid, palmitic acid, stearic acid, behenyl alcohol, cetyl alcohol, eicosanyl alcohol and isocetyl alcohol.

Other examples of oil/emollients include mineral oil, petrolatum, silicone oil such as dimethyl polysiloxane, lauryl and myristyl lactate.

It should be understood that where the emollient may also function as a structurant, it should not be doubly included such that, for example, if the structurant is 15% oleyl alcohol, no more than 5% oleyl alcohol as "emollient" would be added since the emollient (whether functioning as emollient or structurant) never comprises more than 20%, preferably no more than 15% of the composition.

The emollient/oil is generally used in an amount from about 1 to 20%, preferably 1 to 15% by wt. of the composition. Generally, it should comprise no more than 20% of the composition.

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330—Polyquaternium 39; and Jaguar® type conditioners.

Polyethylene glycols which may be used include:

| Polyox | WSR-205 | PEG 14M, |
| Polyox | WSR-N-60K | PEG 45M, or |
| Polyox | WSR-N-750 | PEG 7M. |

Thickeners which may be used include Amerchol Polymer HM 1500 (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the defloculating polymers such as are taught in U.S. Pat. No. 5,147,576 to Montague, hereby incorporated by reference.

Another ingredient which may be included are exfoliants such as polyoxyethylene beads, walnut sheets and apricot seeds.

The liquid compositions, like the bar compositions will have SPF values and lather volume as defined for the bars.

Except in the operating and comparative examples, or where otherwise explicitly indicated, all numbers in this description indicating amounts or ratios of materials or conditions or reaction, physical properties of materials and/or use are to be understood as modified by the word "about".

Where used in the specification, the term "comprising" is intended to include the presence of stated features, integers, steps, components, but not to preclude the presence or addition of one or more features, integers, steps, components or groups thereof.

The following examples are intended to further illustrate the invention and are not intended to limit the invention in any way.

Unless indicated otherwise, all percentages are intended to be percentages by weight.

EXAMPLES

Protocol

In-vitro SPF Measurement for Evaluating Skin Cleansing Compositions Containing Sunscreens This method involves the measurement of the transmission of light across the UV spectrum through a treated substrate. From the transmittance data an estimate of SPF can be obtained.

In-vitro SPF measurements were made on an Optometrics SPF 290 instrument (Optometrics Corp., Ayre Mass., USA). The instrument measures diffuse transmittance through a treated substrate at 5 nm increments covering wavelengths from 290 to 400 nm and reports a calculated SPF. Measurements were taken at 6 sites over a 6.5 cm by 6.5 cm piece of each treated substrate. The substrate used was Vitro-skin™ (IMS Testing Group, Milford, Conn., USA). The Vitro-Skin substrate was pre-hydrated in a desiccator at 80% relative humidity as recommended by the supplier. The vitro-skin substrate was treated by rubbing a wet bar across it 10 times then rubbing the Vitro-skin substrate for 15 seconds. After this the substrate was rinsed under tap water for 15 seconds and blotted dry with a paper towel.

Lather Measurements

Lather was measured using stoppered, graduated 100 ml. cylinders. The cylinders were shaken 10 seconds and foam height observed.

Example 1–4 and Comparative 1–3

The following formulations were made where Table 1 represents formulae containing anionic (water-soluble) UV sunscreens and Table 2 represents formulae containing hydrophobic UV absorbers

TABLE 1

Formulations Containing Anionic (Water-Soluble) UV Absorbers

| Components | Function | Example 1 | Example 2 | Example 3 | Example 4 |
|---|---|---|---|---|---|
| Polyethylene glycol - 8000 | Structurant | 10 | 10 | 10 | 10 |
| Glycerol monostearate | Structurant | 27.6 | 27.6 | 27.6 | 27.6 |
| Palmitic-stearic acid | Structurant | 8.4 | 8.4 | 8.4 | 8.4 |
| Sodium cocoyl isethionate | Surfactant | 27 | 27 | 27 | 27 |
| Cocamidopropyl betaine | Surfactant | 5 | 5 | 5 | 5 |
| Sunflower seed oil | Emollient | — | — | — | 7.5 |
| Petrolatum | Emollient | 16 | 11 | 9 | — |
| Polyqualternium-6 | Skin feel | — | 5 | — | 2.5 |
| Sodium ferulate | Sunscreen | — | — | — | 10 |
| 2-phenlylbenzimidazole-5-sulfonic acid | Sunscreen | 4 | 4 | 4 | — |
| Octocrylene | Sunscreen | — | — | 7 | — |
| Water | | 2 | 2 | 2 | 2 |

TABLE 2

Formulations Containing Only Hydrophobic UV Absorbers

| Components | Function | Comparative 1 | Comparative 2 | Comparative 3 |
|---|---|---|---|---|
| Polyethylene glycol - 8000 | Structurant | 10 | 10 | 10 |
| Propylene glycol | Structurant/Skinfeel | — | — | 13 |
| Paraffin wax | Structurant | — | — | 3 |
| Glycerol monostearate | Structurant | 27.6 | 27.6 | — |
| Palmitic-stearic acid | Structurant | 8.4 | 8.4 | 14 |
| Sodium cocoyl isethionate | Surfactant | 27 | 27 | 30 |
| Sodium stearate | Structurant | — | — | 5 |
| Cocamidopropyl betaine | Surfactant | 5 | 5 | 5 |
| Petrolatum | Emollient | — | 13 | — |
| Sunflower seed oil | Emollient | 7.5 | — | — |
| Polyquaternium-6 | Skin feel | 2.5 | — | 2.5 |
| isononyl ferulate | Sunscreen | 10 | — | — |
| Octyl methoxycinnamate | Sunscreen | — | — | 10 |
| Octocrylene | Sunscreen | — | 7 | — |
| Titanium dioxide | | — | — | 0.5 |
| Miscellaneous salts | | | | 2 |
| Perfume | | | | 1 |
| Water | | 2 | 2 | 4 |

Using the formulations noted, following results were obtained:

| | Example 1 | Example 2 | Example 3 | Example 4 | Comparative 1 | Comparative 2 | Comparative 3 |
|---|---|---|---|---|---|---|---|
| Water soluble anionic sunscreen | | | | | | | |
| (1) Phenylbenzimidazole sulfonic acid | 4.7 SPF | 4.9 SPF | | | | | |
| (2) Sulfonic acid and octycrylene mixture | | | 5.5 SPF | | | | |
| (3) Sodium ferulate | | | | 5.2 SPF | | | |
| Non-water soluble sunscreen: | | | | | | | |
| (1) Isononyl ferulate | | | | | 1.1 SPF | | |
| (2) Octyl | | | | | | | 1 SPF |

-continued

|  | Example 1 | Example 2 | Example 3 | Example 4 | Comparative 1 | Comparative 2 | Comparative 3 |
|---|---|---|---|---|---|---|---|
| methoxycinnamate |  |  |  |  |  |  |  |
| (3) Octycrylene |  |  |  |  |  |  | 1 SPF |

As can be clearly seen from the Table above, where water soluble or mixture of at least one water soluble anionic sunscreen and non-water soluble sunscreen was used, SPF was significantly higher (e.g., 4.7 SPF, 4.9 SPF, 5.5 SPF, 5.2 SPF) compared to when non-water soluble sunscreen was used (e.g., 1.1 SPF, 1 SPF, 1SPF).

Clearly, this is an unexpected selection based on the specific type of sunscreen used.

Example 5

The following liquid formulations were prepared using various anionic surfactant systems and 2-phenyl benzimidazole sulfonic acid as noted below.

TABLE 3

Liquid Compositions Containing Water-Soluble UV Absorbers

| Components | Function | 20% SDS | 20% APG | 20% SLES |
|---|---|---|---|---|
| Sodium dodecyl sulfate | Surfactant | 20 | — | — |
| Alkyl polyglucoside (glucopon 600 UP) | Surfactant | — | 20 | — |
| Sodium lauryl ether sulfate (Steol CA 230) | Surfactant | — | — | 20 |
| 2-phenylbenzimidazole sulfonic acid sodium salt | Sunscreen | 4 | 4 | 4 |
| Water |  | To 100% | To 100% | To 100% |

The following results were obtained:

| Surfactant | SPF |
|---|---|
| 20% SDS | 8.9 |
| 20% APG | 7.7 |
| 20% SLES | 3.4 |

Again, it can be clearly seen that enhanced SPF can be also found in liquid systems.

In comparison, applicants also tested in vitro SPF in a liquid product produced by SKINTEK®, Performance Brands Inc. in Sunrise, Fla. The product is called "Soap Screen®.

The Soap Screen® product contains known "oily" sunscreens, e.g., octyl methoxycinnamate, octyl salicylate and oxybenzone.

When in-vitro SPF was measured it was found to be 1.1, i.e., well below the SPF of sunscreens used in liquids of subject invention.

Example 6

Lather

In order to show less degrading effect on lather by sunscreens of invention compared to more "oily" sunscreens, applicants conducted the following experiment:

Stoppered 100 ml graduated cylinders were prepared. One cylinder (cylinder A) contained 10 ml of 1% sodium lauryl ether sulfate and 1% 2-phenylbenzimidazole-5-sulfonic acid neutralized with a stoichiometric amount of sodium hydroxide and the other (cylimder B) contained 10 ml of 1% sodium lauryl ether sulfate and 1% ethyl hexyl paramethoxy was cinnamate. The cylinders were shaken for 10 seconds, then the foam height was observed. Immediately following shaking both cylinders contained the same volume of foam (approximately 70 ml) but the foam in cylinder B decayed more rapidly than the foam in cylinder A.

| Time (min) | Cylinder A | Cylinder B |
|---|---|---|
| 0 | 70 | 70 |
| 1 | 70 | 55 |
| 5 | 70 | 50 |
| 10 | 65 | 45 |
| 15 | 65 | 35 |
| 20 | 65 | 30 |
| 25 | 65 | 26 |
| 30 | 65 | 20 |

As clearly seen, lather from cylinder B degraded over 30 minutes while degradation in clinder B (with more "soluble" sunscreen of invention) was almost negligible.

What is claimed is:

1. A personal wash bar composition comprising:
   (1) 2 to 80% by wt. first anionic surfactant which is fatty acid or synthetic anionic surfactant;
   (2) 0 to 25% by wt. second surfactant;
   (3) 0 to 15% by wt. free fatty acid;
   (4) 0 to 20% by wt. of a water-soluble structurant which is neither soap nor non-soap detergent and has a melting point in the range 40 to 100° C.; and
   (5) 0.1 to 10% of a sunscreen and/or salt thereof wherein sunscreen and/or salt thereof has SPF from greater than 2 to 25, wherein said sunscreen is selected from the group consisting of phenylbenzimidazole sulphonic acid, anionic salt of phenylbenzimidazole sulphonic acid, mixtures of said sulphonic acid and its anionic salt, ferulic acid, anionic salt of ferulic acid, mixtures of ferulic acid and its anionic salt, and mixtures of said acids and/or their salts, and
   wherein sunscreen agent/salt has solubility of greater than or equal to 0.1% as measured in $H_2O$ at neutral pH: and
   wherein lather generated by said composition degrades no more than 50% after 30 minutes as measured in 100 ml graduated cylinders which have been shaken for 10 seconds.

2. A composition according to claim 1, wherein first surfactant (1) is acyl isethionate and second surfactant (2) is soap.

3. A composition according to claim 1, wherein first surfactant (1) is soap.

4. A compostion according to claim 1, comprising 1 to 20% second surfactant.

5. A compostion according to claim 1, comprising 1–15% free fatty acid.

6. A composition according to claim 1, wherein (4) is polyalkylene glycol.

7. A composition according to claim 1, wherein SPF is 3 to 20.

8. A composition according to claim 7, wherein SPF is 4 to 15.

9. A personal wash liquid composition comprising:
   (1) 10–80% first anionic surfactant;
   (2) 0–15% second surfactant selected from the group consisting of anionic surfactant different from first, amphoteric/zwitterionic surfactant, cationic surfactant and mixtures thereof;
   (3) 0.1 to 10% anionic sunscreen;
   (4) balance water,
   wherein SPF is from greater than 2 to 25; wherein said sunscreen is selected from the group consisting of phenylbenzimidazole sulphonic acid, anionic salt of phenylbenzimidazole sulphonic acid, mixtures of said sulphonic acid and its anionic salt, ferulic acid, anionic salt of ferulic acid, mixtures of ferulic acid and its anionic salt, and mixtures of said acids and/or their salts, and wherein sunscreen agent/salt has solubility of greater than or equal to 0.1% as measured in $H_2O$ at neutral pH; and wherein a lather generated by said composition degrades no more than 50% after 30 minutes as measured in 100 ml graduated cylinders which have been shaken for 10 seconds.

10. A composition according to claim 1, additionally comprising 0 to 40% by wt. $C_{12}$–$C_{14}$ glycerol monoalkanoate.

11. A composition according to claim 10, wherein said glycerol monoalkanoate as glycerol monostearate.

* * * * *